United States Patent
Zulfikar et al.

(10) Patent No.: US 10,799,389 B2
(45) Date of Patent: Oct. 13, 2020

(54) MOUTHPIECE DEVICE FOR THE TREATMENT OF OBSTRUCTIVE SLEEP APNEA SYNDROME

(71) Applicant: BOGAZICI UNIVERSITESI, Istanbul (TR)

(72) Inventors: Sefa Zulfikar, Istanbul (TR); Ozgur Kocaturk, Istanbul (TR); Albert Guvenis, Istanbul (TR)

(73) Assignee: BOGAZICI UNIVERSITESI, Istanbul (TR)

( * ) Notice: Subject to any disclaimer, the term of this patent is extended or adjusted under 35 U.S.C. 154(b) by 365 days.

(21) Appl. No.: 15/739,773

(22) PCT Filed: Jun. 9, 2016

(86) PCT No.: PCT/TR2016/050172
§ 371 (c)(1),
(2) Date: Dec. 25, 2017

(87) PCT Pub. No.: WO2016/209184
PCT Pub. Date: Dec. 29, 2016

(65) Prior Publication Data
US 2018/0177627 A1 Jun. 28, 2018

(30) Foreign Application Priority Data

Jun. 23, 2015 (TR) .............................. a 2015 07715

(51) Int. Cl.
*A61F 5/56* (2006.01)
(52) U.S. Cl.
CPC .................................... *A61F 5/566* (2013.01)
(58) Field of Classification Search
CPC ... A61F 5/56; A61F 5/566; A61C 7/08; A61C 7/36; A61C 9/0006; A61C 17/0211;
(Continued)

(56) References Cited

U.S. PATENT DOCUMENTS

| 3,126,002 A | * | 3/1964 | Owens | A63B 71/085 |
| | | | | 128/861 |
| 5,316,020 A | * | 5/1994 | Truffer | A61F 5/566 |
| | | | | 128/848 |

(Continued)

FOREIGN PATENT DOCUMENTS

WO    0139685 A1    6/2001

OTHER PUBLICATIONS

A. Qureshi et al. "Obstructive sleep apnea", American Academy of Allergy, Asthma and Immunology, 0091-6749, 2003.

(Continued)

*Primary Examiner* — Rachael E Bredefeld
*Assistant Examiner* — Camtu T Nguyen
(74) *Attorney, Agent, or Firm* — Bayramoglu Law Offices LLC

(57) ABSTRACT

A mouthpiece device for the use with the treatment of obstructive sleep apnea syndrome includes at least one main air channel provided at the outlet of the mouth, at least one side air channel provided at the outlet of mouth, at least one one way valve placed inside the main air channel, at least one protective plane arranged between the inner part of the lips and the outer surface of the teeth, at least one palate chamber extending inside the mouth, at least one tongue chamber placed inside the palate chamber, at least one vent provided on the tongue chamber, at least one sensor for measuring the carbon dioxide and oxygen levels in the air exhaled by the patient, at least one palate extension extending from the palate chamber towards the soft palate, and electrically stimulates the palate when the sensor detects that the patient stops breathing.

20 Claims, 5 Drawing Sheets

(58) Field of Classification Search
CPC .............. A61C 19/063; A61C 19/066; A61M 16/0057; A61M 16/0048; A61M 16/0493; A61M 16/0497; A61M 16/0495; A61M 15/0021
USPC .......................................................... 128/848
See application file for complete search history.

(56) References Cited

U.S. PATENT DOCUMENTS

| | | | |
|---|---|---|---|
| 5,792,067 A | | 8/1998 | Karell |
| 5,915,385 A * | | 6/1999 | Hakimi .................. A61F 5/566 128/848 |
| 5,950,624 A * | | 9/1999 | Hart ....................... A61F 5/566 128/200.26 |
| 6,976,491 B2 * | | 12/2005 | D'Agosto ............... A61F 5/566 128/200.24 |
| 8,737,794 B2 * | | 5/2014 | Yamamoto ....... B29D 11/00663 385/130 |
| 2002/0139375 A1 | | 10/2002 | Kulick |
| 2003/0089371 A1 * | | 5/2003 | Robertson ......... A61M 16/0488 128/201.26 |
| 2004/0211430 A1 | | 10/2004 | Pivovarov |

OTHER PUBLICATIONS

M. R. Mannarino et al. "Obstructive sleep apnea syndrome", European Journal of Internal Medicine 23, 2012. p. 586-593.

K. Sutherland et al. "Mandibular advancement splints for the treatment of sleep apnoea syndrome", Swiss Med Wkly. 2011; 141: w13276.

S. A. Deane et al. "Comparison of Mandibular Advancement Splint and Tongue Stabilizing Device in Obstructive Sleep Apnea: A Randomized Controlled Trial", Sleep, vol. 32, No. 5, 2009.

Elshaug AG et al, "An analysis of the evidence-practice continuum: is surgery for obstructive sleep apnoea contraindicated?", J Eval Clin Pract. Feb. 2007;13(1):3-9.

* cited by examiner

MOUTHPIECE DEVICE FOR THE TREATMENT OF OBSTRUCTIVE SLEEP APNEA SYNDROME

CROSS REFERENCE TO RELATED APPLICATIONS

This application is the national phase entry of International Application PCT/TR2016/050172, filed on Jun. 9, 2016, which is based upon and claims priority to Turkish Patent Application No. 2015/07715, filed on Jun. 23, 2015, the entire contents of which are incorporated herein by reference.

FIELD OF THE INVENTION

The present invention relates to a silent, portable, novel mouthpiece device which neither requires any surgical intervention, nor covers the face of patients' thus causes no discomfort, and which is for the use with the treatment of obstructive sleep apnea syndrome.

BACKGROUND OF THE INVENTION

Obstructive sleep apnea syndrome (OSAS) is characterized by repeated cycles of complete or partial upper airway obstruction due to the pharyngeal collapse during sleeping. Airway obstruction that may occur many times during night results in reduced sleep quality of individual due to not getting required level of oxygen. Obstructive sleep apnea syndrome can directly or indirectly cause health problems. Some of the consequences can be listed as chronic fatigue, headaches, excessive daytime sleepiness, hypertension, stroke, neurocognitive disorders, increased prevalence of motor vehicle accidents and occupational accidents.

The main treatment options for obstructive sleep apnea syndrome are surgical operations, continuous positive airway pressure devices and oral appliances such as mandibular repositioning devices (MRD) and tongue retaining devices (TRD). These treatment options may cause serious adverse events for the patients.

CPAP device supplies a steady stream of pressurized air to patients' airway in order to keep the airway open. Continuous positive airway pressure (CPAP) is considered as the first line therapy for patients diagnosed with obstructive sleep apnea. However, patient compliance is disappointingly below expectations due to several disadvantages.

Some of the disadvantages of CPAP devices can be listed as follows: unable to have a comfortable sleep position due to a nasal, oral or an oronasal interface, noise level produced by CPAP device, not being a portable device, nasal congestion, dryness, rhinorrhea, gastric distension and facial irritation.

Mandibular repositioning devices (MRD) are the apparatuses used for holding the mandible in an advanced position with respect to the resting position, and thus enabling the soft palate to move together with the mandible and increasing the dimensions of upper airway. Several disadvantages are temporomandibular joint discomfort, potentially permanent altered bite, tooth pain and headaches. These relatively minor side effects may result in anatomical changes with continued use of appliance.

The tongue retaining devices (TRD) aim to retain the tongue in forward, upper or lower position other than its normal position via friction or vacuum application and prevent the airway obstructions. The major limitation of tongue retaining devices via constant vacuum appears to be involuntarily loss of the constant vacuum due to moving tongue while gulping or with other reasons. Other side effects caused by constant vacuum are soft tissue irritation, swelling and edema. Several designs using this method also do not allow oral inhalation of patient which makes the treatment dysfunctional for the patients who are not able to inhale through nose.

Surgical modifications as treatment option include highly invasive techniques such as soft tissue reduction, maxillamandibular or tongue repositioning and tube/stent implantation into soft palate in order to harden the soft tissue. This approach does not provide high success rate for the treatment of disease as well as it has certain operational risks as any other surgery. Moreover, a possible damage caused by surgery would be irreversible. Potential speech impairment and gulping problems are only some of the adverse events.

To date, it has not been developed any mouthpiece device which provides ease of use and comfort while efficiently treating obstructive sleep apnea syndrome.

The United States patent document numbered U.S. Pat. No. 5,792,067A discloses an electromuscular stimulator that effects a beneficial medical purpose selected from the group consisting of mitigating snoring, mitigating obstructive sleep apnea, mitigating hypertension, dental analgesia, general analgesia, monitoring physiological conditions and facilitating the intraoral delivery of medication is disclosed. The electromuscular stimulator includes a first electrode for making electrical contact with a first anatomical structure; a second electrode for making electrical contact with a second anatomical structure; a control unit operably connected to the first and second electrodes; and a means for positioning the first and second electrodes relative to the first and second anatomical structures, respectively.

SUMMARY OF THE INVENTION

The objective of the present invention is to provide a portable device which used in treatment of obstructive sleep apnea.

Another objective of the present invention is to provide a device which is designed as a mouthpiece device so that it does not cover the patient's overall face and only uses the mouth volume therefore providing sleep comfort.

Yet another objective of the present invention is to provide a device which does not make high decibel noise during use.

A further objective of the present invention is to provide a device which aims to prevent the mandible to collapse backwards contrary to the devices which aims to pull the mandible forward by force.

Another objective of the present invention is to provide a device which has a mechanism using the dynamic vacuum created only by the patient's breath, and preventing the tongue to fall back towards the larynx thanks to the structure of its tongue chamber.

Yet another objective of the present invention is to provide a device comprising a biocompatible polymer which can be shaped specific to individual so that upper and lower teeth can easily fit.

A further objective of the present invention is to provide a device which enables the airway to remain open at all times by increasing the pressure in mouth at a desired level.

Another objective of the present invention is to provide a device comprising sensors which continuously control breathing, measure oxygen and carbon dioxide levels, and thus enabling to follow the patient's sleep quality.

Yet another objective of the present invention is to provide a device which sends a warning signal that can wake the patient by interacting with smartphone software when the sensors detect that breathing stops.

A further objective of the present invention is to provide a device which warns the patient without waking him/her up with small electrical impacts when the sensors detect that breathing stops.

Figure 1:
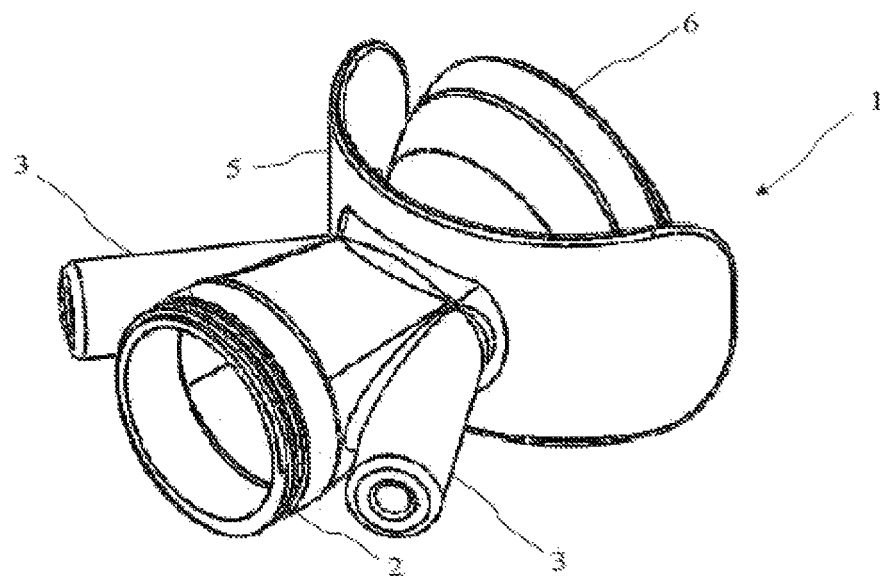
FIG. 1 is the front perspective view of the inventive device.
Figure 2:
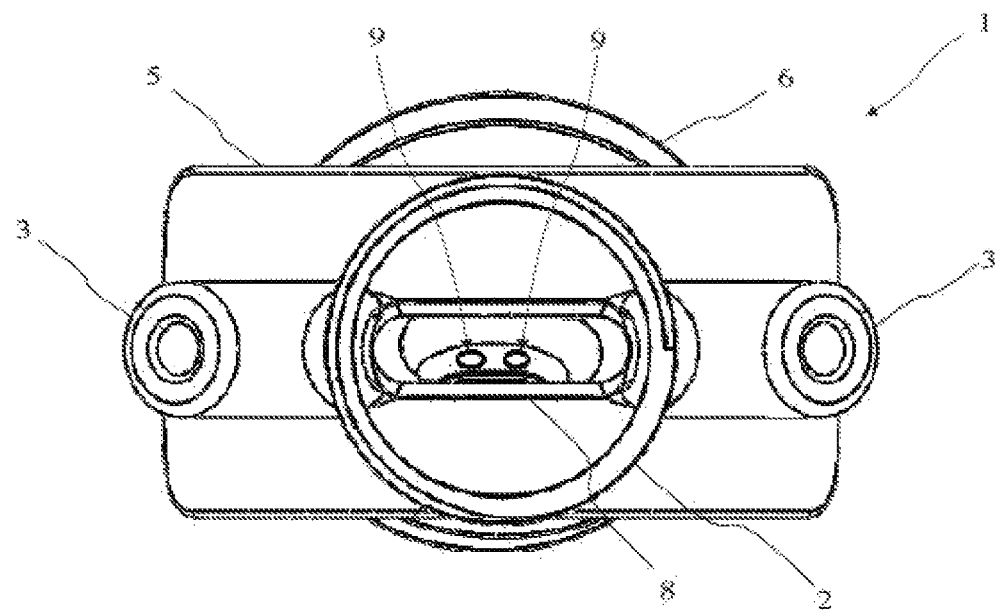
FIG. 2 is the front view of the inventive device.
Figure 3:
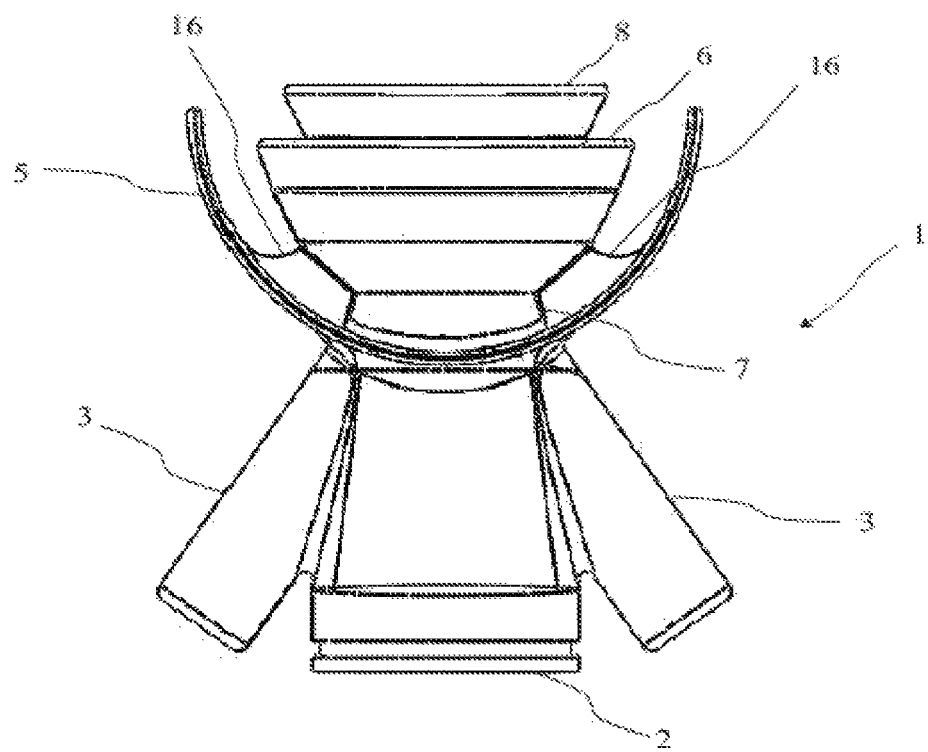
FIG. 3 is the top view of the inventive device.
Figure 4:
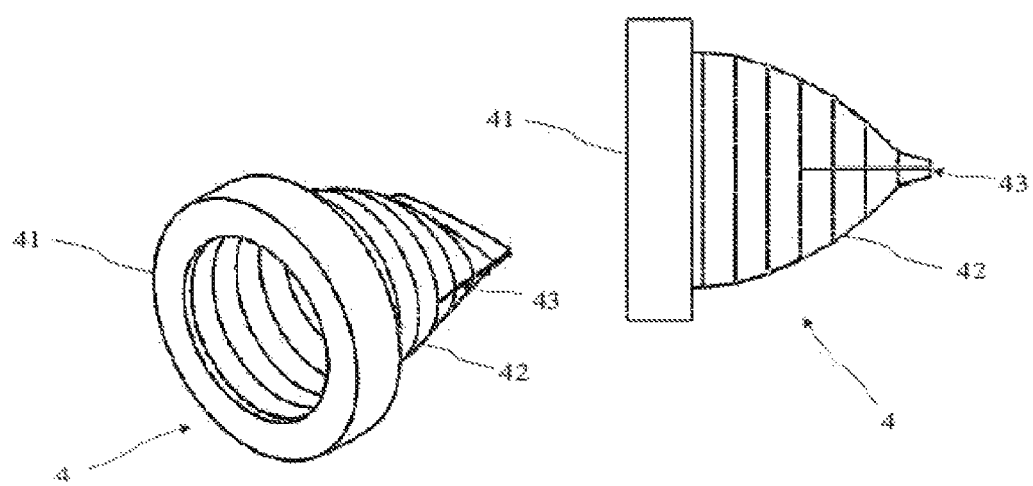
FIG. 4 is the perspective and lateral view of the one way valve presents in the inventive device.
Figure 5:
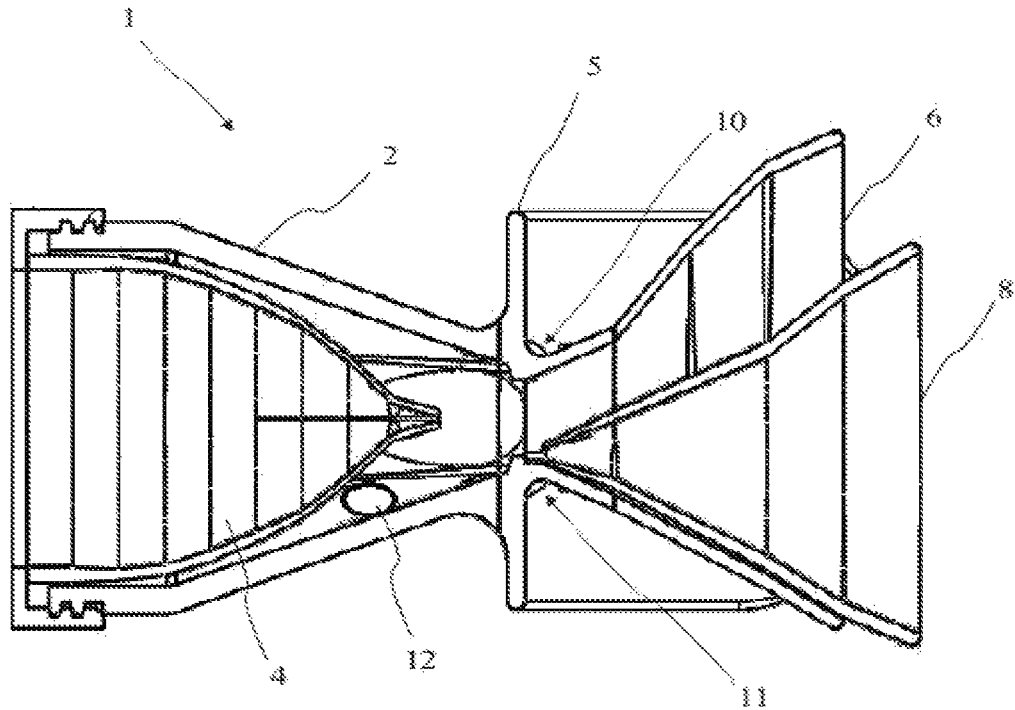
FIG. 5 is the lateral cross-sectional view of an embodiment of the inventive device comprising valve and sensor.

The components shown in the figures are each given reference numbers as follows:

17. Mouthpiece device
18. Main air channel
19. Side air channel
20. One way valve
  41. Valve lid
  42. Valve body
  43. Air Opening
21. Protective plane
22. Palate chamber
23. Narrow pass
24. Tongue chamber
25. Vent
26. Upper teeth cover
27. Lower teeth cover
28. Sensor
29. Palate extension
30. Aperture
31. Adjustment pin
32. Support column

DETAILED DESCRIPTION OF THE EMBODIMENTS

The inventive mouthpiece device (1) for treatment of obstructive sleep apnea essentially includes at least one main air channel (2) which is provided at the outlet of the mouth and enables air passage into the mouth, at least one side air channel (3) which is provided at the outlet of mouth for supporting the main air channel (2), and which enables air passage into the mouth and air discharge outside the mouth, at least one one way valve (4) which is placed inside the main air channel (2), and only allows air passage by preventing air discharge from the main air channel (2), at least one protective plane (5) which is between the inner part of the lips and the outer surface of the teeth, at least one palate chamber (6) which extends inside the mouth by widening in the rear part of the protective plane (5), at least one narrow pass (7) wherein the main air channel (2) and the side air channel (3) combine and connect to the palate chamber (6), at least one tongue chamber (8) which is placed inside the palate chamber (6), at least one vent (9) which is provided on the tongue chamber (8) and creates vacuum effect inside the mouth, at least one upper teeth cover (10) which is between the protective plane (5) and the palate chamber (6), on which the upper teeth of the patient fit, at least one lower teeth cover (11) which is between the protective plane (5) and the palate chamber (6), on which the lower teeth of the patient fit, at least one sensor (12) which measures the carbon dioxide and oxygen rates in the air exhaled by the patient, and controls breathing, at least one palate extension (13) which extends from the palate chamber (6) towards the soft palate, and which electrically stimulates the palate when the sensor (12) detects the patient stops breathing, at least one support column (16) which is placed behind the protective plane (5), and which protects the structural integrity of the narrow pass (7) against the pressure created by the teeth by surrounding it.

In one embodiment of the invention, there are two side air channels (3) placed around the main air channel (2). The one way valve (4) present inside the main air channel (2) allows air passage through the main air channel (2) as well as through the side air channels (3) during breathing of the patient. However, while the patient is exhaling, the one way valve (4) closes the air exit through the main air channel (2) and breath exit occurs only through the side air channels (3). Due to difference created by the use of valve (4), the patient can exhale in a longer time than exhaling without the device (1), and thus the air way is enabled to remain open by increasing pressure in the mouth during this time.

In the preferred embodiment of the invention, main air channel (2) and the side air channel (3) is cylindrical.

The one way valve (4) has at least one valve lid (41) which has a structure enabling mounting inside the main air channel (2), at least one valve body (42) which has a conical structure on its lateral cross section, at least one air opening (43) which is positioned inside the narrow pass (7), through which the air passes during breathing and which is closed for air passage during exhaling.

Figure 6:
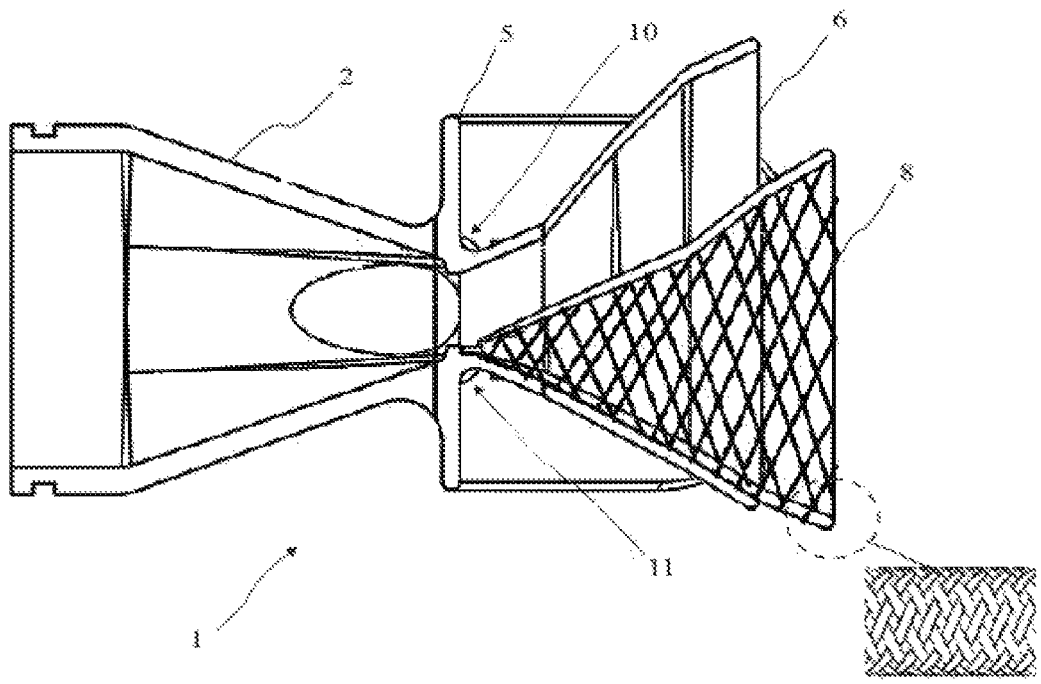
FIG. 6 is the lateral cross-sectional view of an embodiment of the inventive device not comprising valve but comprising tongue chamber formed of biaxial weaving.
Figure 7:
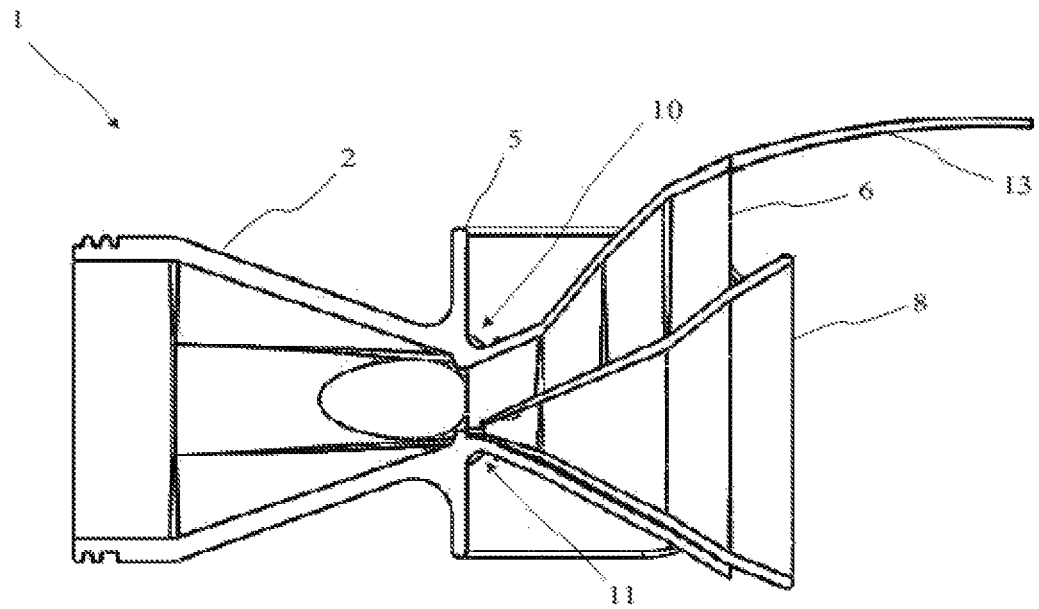
FIG. 7 is the lateral cross-sectional view of an embodiment of the inventive device not comprising valve, but comprising extension which provides electrical stimulation.

The one way valve (4) is preferably used inside the device (1), and it can be detachable and changeable. After it gets dirty or shelf life expires, it can be replaced with the new one. The one way valve (4) is fixed inside the main air channel (2) by rotating via a screw system (FIG. 1) on the valve lid (41) or with a mechanical click-fit lock system (FIG. 6). Furthermore, in order to ease the breathing of the patient, exhaling and/or humidifying drugs can be loaded on the one way valve (4).

The protective plane (5) completely covers the teeth and enables the device (1) to fit into the mouth and tightened with the lips. Upper teeth cover (10) and lower teeth cover (11) provided right behind the protective plane (5) enable the device (1) to fit into the mouth. In one embodiment of the invention, the upper teeth cover (10) and the lower teeth cover (11) are made of same material, and they are formed of biocompatible polymer material which gets softer by heat and/or which can take form when it is bitten such that it will be compatible with different mouth structures. By means of the upper teeth cover (10) and the lower teeth cover (11), it is possible to increase airway volume by keeping the mouth in biting position without needing a mechanism which pulls the mandible of the patient forward.

The palate chamber (6) is a structure which completely covers inside the mouth, the upper part of which is in contact with the hard palate, and the lower part of which is positioned under the tongue, and which aims to increase the volume inside the mouth.

The tongue chamber (8) is a structure which keeps the tongue in its normal position and prevents it from falling back towards to the soft palate.

Figure 8:
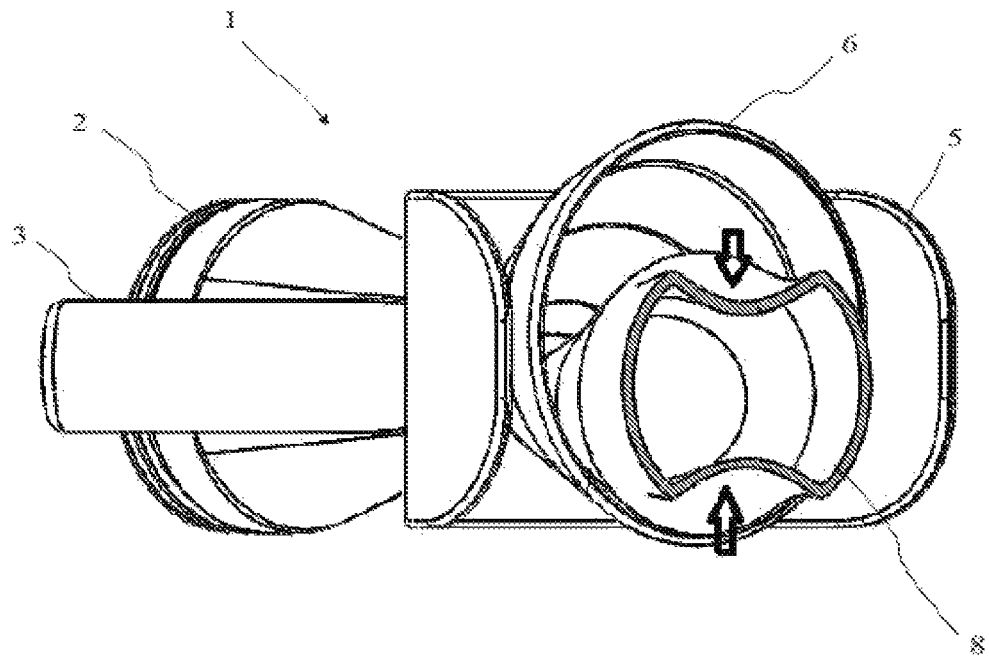
FIG. 8 is the rear perspective view of an embodiment of the inventive device not comprising valve, but comprising tongue chamber formed of scissors mechanism provided with shape memory metal.
Figure 9:
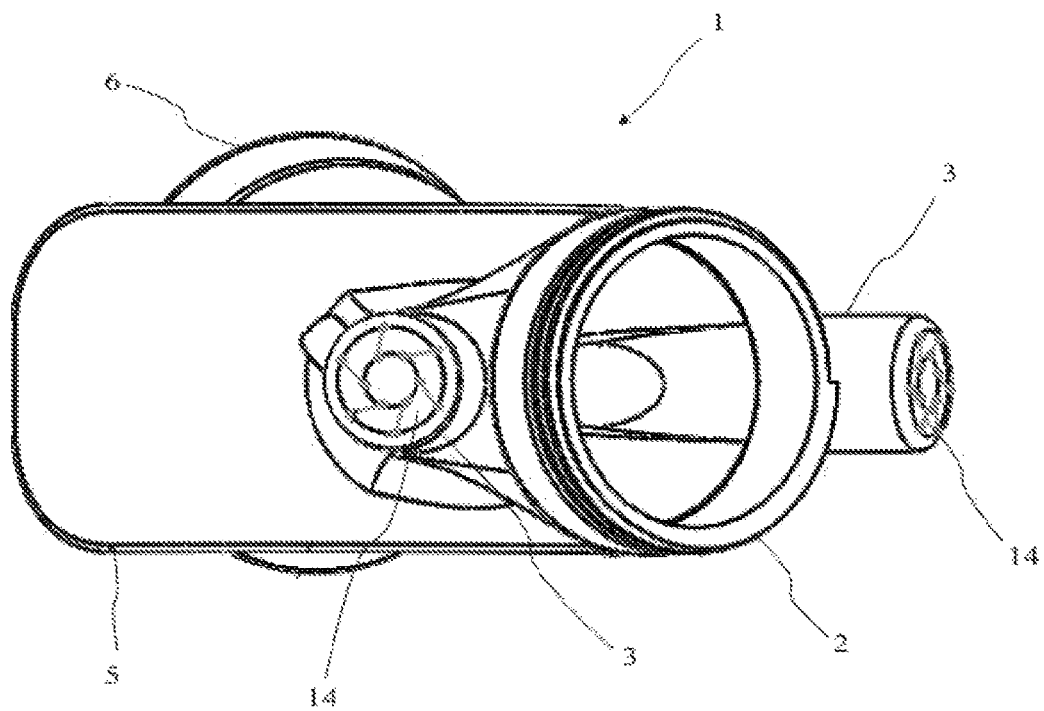
FIG. 9 is the perspective view of the aperture present in one embodiment of the inventive device on the side air channel.
Figure 10:
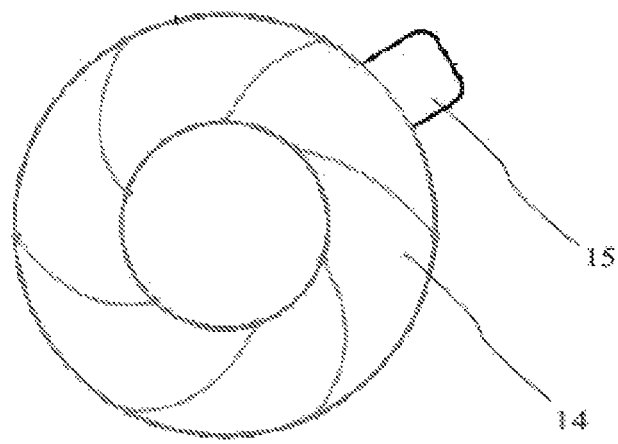
FIG. 10 is the front view of the aperture present in one embodiment of the inventive device.

In one embodiment of the invention, the tongue chamber (8) is comprised of a scissors mechanism provided with shape memory metal. This system slightly applies pressure to the tongue and keeps the tongue in its normal position. The said application and the direction of the mechanic pressure is shown in FIG. 8.

In another embodiment of the invention, the tongue chamber (8) is comprised of a biaxial woven structure manufactured from metal or polymeric material. The said structure is formed by wrapping the metal or polymer strips biaxially. In this embodiment of the invention, the tongue is not continuously subjected to pressure; it is held dynamically and prevented from falling back. The said application is shown in FIG. 6.

The vent (9) aims to create a dynamic vacuum effect inside the mouth by using patient's own breath without requiring a separate vacuum system attached to the device (1), and thus the tongue is prevented from falling back. By means of this mechanism, the patient can easily gulp, and it does not cause problems such as swelling, edema, and irritation in the tongue since the vacuum is applied dynamically. In the preferred embodiment of the invention, there are two vents (9).

The sensor (12) is a member which measures carbon dioxide and/or oxygen ratio, which can detect when the user stops breathing, and record inhaling-breathing times. The data recorded by the sensor (12) can be transferred wirelessly to a smart device software, and the patient can see their sleep quality through the night preferably in graphic via the display. In case the patient stops breathing, sensor (12) enables to wake the patient by warning signal by means of the smart device to which it is connected. Therefore, the patient can have the opportunity to track and compare sleep quality in different nights. In a preferred embodiment of the invention, the sensor (12) can preferably be any place on the side air channel (3).

The palate extension (13) is a member providing mechanical support for the soft palate and preventing the soft palate from collapsing.

In a preferred embodiment of the invention, the palate extension (13) operates in coordination with the sensor (12), and prevents the soft palate from collapsing by giving electrical stimulation on the soft palate tissue on which it is present such that it will not wake the patient when it is detected that the patient stops breathing. The palate extension (13) is preferably detachable and changeable, and it is made of a material which allows being used by adhering on the soft palate.

In one embodiment of the invention, the aperture (14) which is located on at least one side air channel (3) can be widened and narrowed via adjustment pin (15) located thereon in order to adjust the exiting speed of the breath exhaled by the patient. In a preferred embodiment of the invention, the aperture (14) is circular and it narrows and widens in diameter. Upon narrowing the aperture (14), the exhaling time of the patient is elongated, and thus increase in pressure in the mouth is controlled. After the airway volume of the patient is examined via magnetic resonance imaging technique, air exit speed determined by the doctor for the patient is calculated, and it can be adjusted by means of the adjustment pin (15) on the aperture (14). By this means, the user can be treated with a special treatment for themselves depending on the intensity of their disease.

The inventive mouthpiece device (1) for treatment of obstructive sleep apnea enabling the airway to remain open all the time by increasing pressure inside the mouth and oropharynx volume only covers the mouth volume of the patient, and it allows comfortable sleep since it does not cover any other area on the face except this. Furthermore, it is portable since it does not require any additional mechanism or connection, and it does not make any noise during use. It improves the situation of the patient in case of continuous use.

What is claimed is:

1. A mouthpiece device for treatment of obstructive sleep apnea comprising:
   at least one main air channel is configured to be provided at an outlet of a mouth and enables air to passage into the mouth,
   at least one protective plane is configured to be arranged between an inner part of a patient's lips and an outer surface of the patient's teeth,
   at least one sensor is configured to measure a carbon dioxide rate and an oxygen rate in the air exhaled by a patient, and controls breathing,
   at least one palate extension is configured to electrically stimulate the palate when the sensor detects that the patient stops breathing,
   at least one side air channel is configured to be provided at the outlet of the mouth for supporting the main air channel and configured to enable air to passage into the mouth and to discharge outside the mouth;
   at least one one way valve which is placed inside the main air channel and only allows an air passage by preventing air discharging from the main air channel,
   at least one palate chamber is configured to extend inside the mouth and the at least one palate extension is configured to extend from the at least one palate chamber towards the soft palate,
   at least one narrow pass, wherein the main air channel and the side air channel are combined and connected to the palate chamber,
   at least one tongue chamber which is placed inside the palate chamber,
   at least one vent is configured to be provided on the tongue chamber and configured to create a vacuum effect inside the mouth,
   at least one upper teeth cover which is arranged between the protective plane and the palate chamber, wherein the upper teeth cover is configured to fit with the upper teeth of the patient, at least one lower teeth cover which is between the protective plane and the palate chamber, wherein the lower teeth cover is configured to fit with the lower teeth of the patient, at least one support column which is placed behind the protective plane and configured to protect a structural integrity of the narrow pass against a pressure created by the teeth by surrounding the narrow pass.

2. A mouthpiece device for treatment of obstructive sleep apnea comprising:

at least one main air channel is configured to be provided at an outlet of a mouth and enables air to passage into the mouth;

at least one protective plane is configured to be arranged between an inner part of a patient's lips and an outer surface of the patient's teeth;

at least one side air channel is configured to be provided at the outlet of mouth for supporting the main air channel and configured to enable air to passage into the mouth and to discharge outside the mouth;

at least one one way valve which is placed inside the main air channel, and only allows an air passage by preventing air discharging from the main air channel;

at least one palate chamber is configured to extend inside the mouth by widening in a rear part of the protective plane;

at least one narrow pass, wherein the main air channel and the side air channel are combined and connected to the palate chamber;

at least one tongue chamber which is placed the at least one palate chamber;

at least one upper teeth cover which is arranged between the protective plane and the palate chamber, wherein the upper teeth cover is configured to fit with the upper teeth of the patient;

at least one lower teeth cover which is arranged between the protective plane and the palate chamber, wherein the lower teeth cover is configured to fit with the lower teeth of the patient;

at least one support column which is placed behind the protective plane and configured to protect a structural integrity of the narrow pass against a pressure created by the patient's teeth surrounding the narrow pass.

3. The mouthpiece device for the treatment of obstructive sleep apnea according to claim 2, further comprising at least one sensor that is configured to measure a carbon dioxide rate and an oxygen rate in the air exhaled by the patient, and controls breathing.

4. The mouthpiece device for the treatment of obstructive sleep apnea according to claim 3, further comprising at least one palate extension that is configured to electrically stimulate the palate when the sensor detects that the patient stops breathing and extends from the palate chamber towards the soft palate.

5. The mouthpiece device for the treatment of obstructive sleep apnea according to claim 3, wherein the sensor is configured to record exhaling-inhaling times of the patient and wirelessly transfer recorded data to a smart device software, so that the mouthpiece device is configured to enable the patient to track sleep quality during night.

6. The mouthpiece device for the treatment of obstructive sleep apnea according to claim 4, wherein the at least one palate extension provides a mechanical support wherein the mechanical support is configured to be on the soft palate tissue such that the mouthpiece device would not wake the patient up.

7. The mouthpiece device for the treatment of obstructive sleep apnea according to claim 4, wherein the palate extension is detachable and replaceable.

8. The mouthpiece device for the treatment of obstructive sleep apnea according to claim 3, wherein the sensor is configured to record exhaling-inhaling times of the patient and wirelessly transfer recorded data to a smart device software, so that the mouthpiece device enables the patient to be woken up via the smart device to which the patient is connected in case where the patient stops breathing.

9. The mouthpiece device for the treatment of obstructive sleep apnea according to claim 2, wherein the one way valve is detachable and replaceable.

10. The mouthpiece device for the treatment of obstructive sleep apnea according to claim 9, the one way valve is configured to enable the patient to exhale in longer time than exhaling without the mouthpiece device and thus configured to enable an airway to remain open by increasing a pressure in the mouth during this time, wherein the mouthpiece device further comprises:

at least one valve lid which has a structure enabling being mounted inside the main air channel, at least one valve body wherein a conical structure is arranged on a lateral cross section of the valve body, and at least one air opening which is positioned inside the narrow pass, wherein the air passes through the air opening during breathing and the air opening is closed for an air passage during exhaling.

11. The mouthpiece device for the treatment of obstructive sleep apnea according to claim 2, wherein an inhaling and/or humidifying drug is loaded on the one way valve to be configured to ease the breathing of the patient.

12. The mouthpiece device for the treatment of obstructive sleep apnea according to claim 2, wherein the protective plane enable the mouthpiece device to be configured to fit into the mouth by completely covering the patient's teeth and to be configured to tighten with the patient's lips.

13. The mouthpiece device for the treatment of obstructive sleep apnea according to claim 2, wherein the upper teeth cover and the lower teeth cover are placed right behind the protective plane, and manufactured from biocompatible polymer material that gets softer by heat and/or takes form when the upper teeth cover and the lower teeth cover are bitten such that the upper teeth cover and the lower teeth cover will be compatible with different mouth structures.

14. The mouthpiece device for the treatment of obstructive sleep apnea according to claim 2, wherein the upper teeth cover and the lower teeth cover are configured for enabling to increase an airway volume by keeping the mouth in a biting position without requiring a mechanism pulling the mandible of the patient forward.

15. The mouthpiece device for the treatment of obstructive sleep apnea according to claim 2, wherein the tongue chamber is configured to prevent the tongue from falling towards the soft palate by keeping the tongue in a normal position.

16. The mouthpiece device for the treatment of obstructive sleep apnea according to claim 15, wherein at least one vent is provided on the tongue chamber and is configured to create a vacuum effect inside the mouth.

17. The mouthpiece device for the treatment of obstructive sleep apnea according to claim 15, wherein the tongue chamber is formed of a metal scissors system which is provided with memory and the tongue chamber is configured to keep the tongue in a normal position by applying a mechanic pressure on the tongue.

18. The mouthpiece device for the treatment of obstructive sleep apnea according to claim 15, wherein the tongue chamber comprises a biaxial woven structure manufactured with metal or polymeric material, and the tongue chamber is configured to prevent the tongue from falling back by dynamically holding the tongue without subjecting the tongue to a continuous pressure.

19. The mouthpiece device for the treatment of obstructive sleep apnea according to claim 2, wherein an aperture is presented on the at least one side air channel, the aperture is enabled to be widened and narrowed with an adjustment pin provided thereon in order to adjust an exhaling speed of the patient.

20. The mouthpiece device for the treatment of obstructive sleep apnea according to claim 19, wherein an opening of the aperture is adjusted according to an air exiting speed considered suitable for the patient by a doctor after an airway volume of the patient is examined with a magnetic resonance imaging technique.

* * * * *